United States Patent [19]

Frank

[11] Patent Number: 4,475,382

[45] Date of Patent: Oct. 9, 1984

[54] APPARATUS FOR MONITORING ENGINES

[75] Inventor: Peter Frank, London, England

[73] Assignee: Frank & Ockrent Limited, London, England

[21] Appl. No.: 400,417

[22] Filed: Jul. 21, 1982

[30] Foreign Application Priority Data

Jul. 21, 1981 [GB] United Kingdom ............... 8122360

[51] Int. Cl.³ .......................................... G01M 15/00
[52] U.S. Cl. .................................... 73/116; 340/627; 356/343
[58] Field of Search ............... 250/301, 373, 565, 574; 73/116; 340/627; 184/1 C; 356/342, 339, 338

[56] References Cited

U.S. PATENT DOCUMENTS 2,907,993 10/1959 Mathisen ............................ 340/627
3,202,826 8/1965 Greathouse ..................... 356/343 X
3,358,148 12/1967 Conklin et al. ................. 356/343 X

FOREIGN PATENT DOCUMENTS 1129402 10/1968 United Kingdom .
1200307 7/1970 United Kingdom .

OTHER PUBLICATIONS

Developments in Crankcase Oil-mist Detector, from Engineering, vol. 184, Sep. 1957, London, pp. 303–305.

Primary Examiner—Jerry W. Myracle
Attorney, Agent, or Firm—Robert Scobey

[57] ABSTRACT

Oil mist detecting apparatus comprises a measuring chamber which receives air, and oil mist if present, from an engine compartment. The apparatus includes a radiation source which emits light into the measuring chamber, and the radiation sensor which is so disposed as to receive light scattered by oil mist in the chamber. A second radiation source is preferably provided for testing purposes, the second source being arranged to emit radiation directly to the sensor.

10 Claims, 1 Drawing Figure

APPARATUS FOR MONITORING ENGINES

FIELD OF THE INVENTION

This invention relates to apparatus for monitoring the condition of internal combustion engines and particularly but not exclusively to detection of liquid mists in the crankcase compartments of an engine.

The invention is particularly applicable to oil mist detectors. These are used to detect faults in internal combustion engines which result in overheating and the generation of oil mist in a crankcase compartment. Such detectors are of particular value in monitoring the condition of large diesel engines, for example 2-stroke marine engines.

DESCRIPTION OF PRIOR ART

One known form of oil mist detector is capable of detecting oil mist in any of several crankcase compartments of an engine. The apparatus comprises conduits leading from each of the crankcase compartments to a common rotary valve. The valve successively connects each of the conduits to a measuring tube. Light is shone through the tube and the amount of light transmitted is measured.

If oil mist is generated in any one of the crankcase compartments, then when the conduit leading to the compartment is connected to the measuring tube the generated oil mist which reaches the measuring tube reduces the amount of light transmitted through the tube. This produces an electrical signal which can be used to generate an alarm and/or stop the engine. The operation of the rotary valve is stopped so that the faulty compartment continues to be monitored.

To achieve a sufficiently accurate measurement, the amount of light transmitted through the tube is compared with that transmitted through a reference tube provided with its own separate light source and sensor.

The measuring and reference tubes have to be long, and accurately designed, to ensure that the generated oil mist has a significant effect on the light transmissivity. The photocells used to detect the light transmitted through the tubes have to be accurately matched.

The entire apparatus is very expensive and quite slow in operation. Installation has to be carried out rather carefully to ensure that there is no possibility of oil collecting in the conduits leading from the crank case compartments to the rotary valve. This requirement also places restrictions on the location and design of the equipment. The use of moving parts in the apparatus, particularly the rotary valve, results in added expense both in manufacture and servicing. Also, if a fault is detected in one crankcase compartment, the monitoring of the other crankcase compartments is terminated.

SUMMARY OF INVENTION

In accordance with one aspect of the present invention there is provided an oil mist detector operable to detect the presence of oil mist in an engine compartment by measuring radiation reflected from the oil mist. The detector may be disposed actually inside a crankcase compartment, but preferably it detects the mist in a measuring compartment connected to receive air from the engine compartment.

An oil mist detector according to the present invention thus relies on a different property of the oil mist, namely its ability to scatter light, rather than its opacity. It has been found that this has the advantage that the measurement of light reflected from oil mist, rather than measuring the reduction in light transmissivity due to the presence of oil mist, provides substantially increased sensitivity. Consequently, the measuring compartment, if provided, need only be relatively small and therefore inexpensive compared to the known types of detector discussed above.

Further, it has been found that there is no requirement for the reference tube used in the prior art; this, it is believed, is partly due to the increased sensitivity of the apparatus, and partly because in the prior art the reference tube was required to indicate the amount of illumination of the sensor to be expected when no oil mist is present. In the present invention, there is substantially no illumination of the sensor when there is no oil mist present, and accordingly this particular function of the reference tube is no longer required.

Another advantage associated with the present invention is that the presence of oil deposits on the radiation source or sensor does not have such a serious effect on the sensitivity of the apparatus. This is because, in the prior art, any decrease in the amount of illumination of the sensor was associated with a very substantial alteration in the amount of oil mist; in the present invention, a change in the amount of oil mist causes a relatively greater change in the sensor output, and, conversely, an alteration in the sensor output due to oil deposits corresponds to a relatively smaller change in the amount of oil mist.

The apparatus is therefore more reliable, which is particularly important in the context of monitoring oil mist in engines as conditions leading to excess oil mist can have very serious consequences. Also, the apparatus is very economical to produce because it does not require accurately manufactured and accurately matched components.

Advantageously, because the apparatus can be made inexpensively, it is economical to provide a separate detector for each of the crank case compartments. The detector can be made very small, thereby simplifying installation.

Using a separate detector for each crankcase compartment has the advantage that the rotary valve of the prior art is not required, thereby further reducing costs and avoiding the need for moving parts. In addition, this also allows continuous monitoring of each crankcase compartment, so that even when a fault is detected in one of the compartments, the remaining compartments continue to be monitored, thereby providing a safer and more reliable system.

The invention thereby provides, in an independent aspect, apparatus for monitoring the condition of an engine having a plurality of crankcase compartments, the apparatus comprising a plurality of detectors each operable to provide a signal in response to the detection of oil mist in a respective crankcase compartment. Each detector preferably operates by detecting light reflected from the oil mist, in accordance with the first-mentioned aspect of the invention.

Each of the detectors preferably has a measuring compartment which receives air and, if present, oil mist from its respective crankcase compartment. The apparatus may be provided with a common fan for drawing the air through all the measuring compartments from the respective crankcase compartments.

When using a detector to monitor an engine, it is desirable to provide some means for checking that the detector is operating correctly, and for providing an alarm in the event of a malfunction. Thus, in accordance with a further aspect of the invention, a detector for detecting the presence of oil mist generated in an engine has a radiation sensor operable to provide a signal indicating the presence of the mist in accordance with the amount of radiation received from a first radiation source, the detector further including a second radiation source which is operable, preferably directly, to illuminate the radiation sensor irrespective of the presence of the mist or spray. Preferably, the detector comprises means for automatically operating the second radiation source at regular intervals, and for providing a signal indicating a malfunction of the detector if the radiation sensor does not provide a signal in response to the radiation received from the second source.

The term "radiation" as used herein is intended to cover radiation in any part of the electromagnetic spectrum, and is not restricted to visible radiation. In preferred embodiments of the invention, infra-red radiation sources are used.

BRIEF DESCRIPTION OF DRAWING

An arrangement embodying the invention will now be described by way of example with reference to the accompanying FIG. 1, which schematically shows an oil mist detector in accordance with the invention.

DETAILED DESCRIPTION OF PARTICULAR EMBODIMENT

Figure 1:
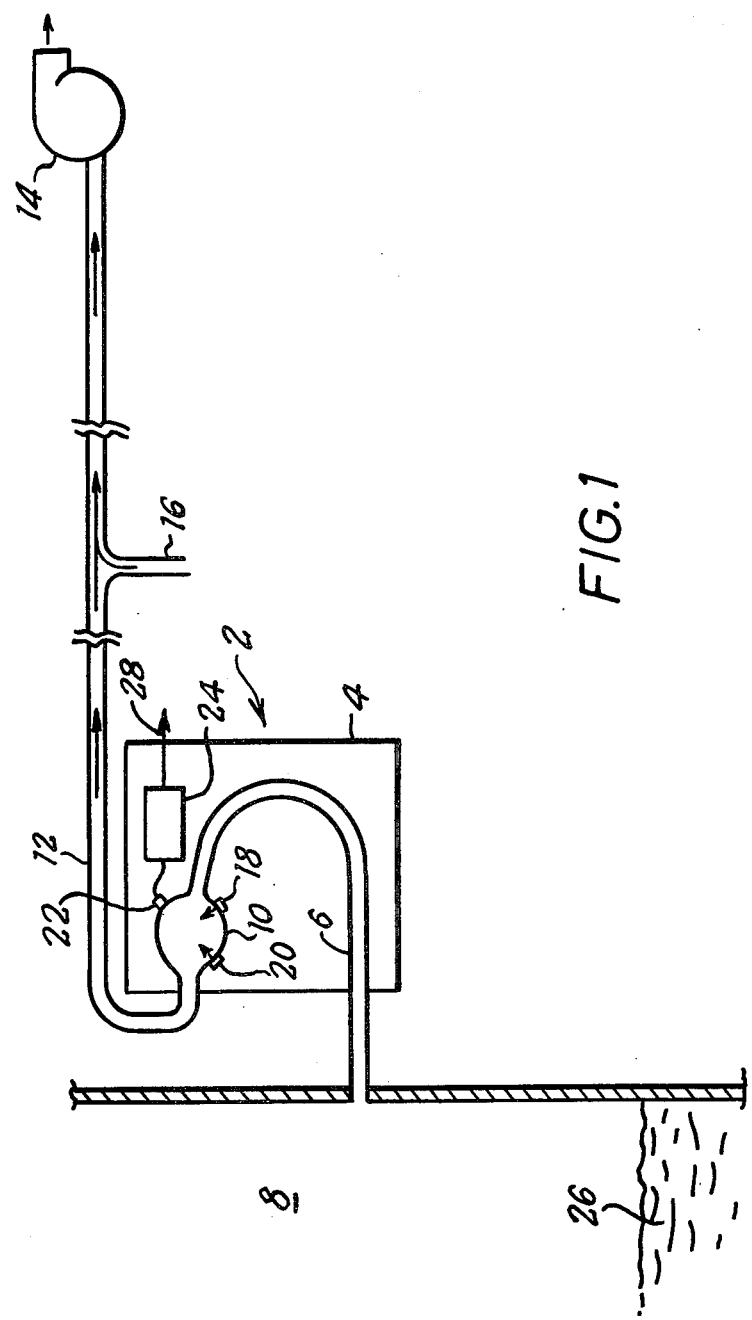

Referring to FIG. 1, the oil mist detector 2 comprises a box 4 which is sealed and has a dark-coloured interior to help prevent incoming or reflected light from affecting the operation of the detector. The oil mist detector 2 further comprises a measuring compartment 10 which is connected to a conduit 6 which leads out of the box 4 and extends for a short distance before leading to the interior of a crankcase compartment 8.

The measuring compartment 10 is also connected to an outlet passage 12 leading to a fan 14. The fan 14 draws air from the crankcase compartment 8 through the conduit 6, the measuring compartment 10 and the outlet passage 12.

The outlet passage 12 has several branch passages, one of which is indicated at 16, leading to other detectors (not shown) for detecting oil mist in other crankcase compartments of the engine being monitored. The fan 14 is operable to draw air through each crankcase compartment being monitored.

The detector 2 also includes two infra-red light sources, a main source 18 and a test source 20 which are arranged to direct light into the measuring compartment 10 in generally mutually transverse, preferably perpendicular, directions. The detector 2 further includes a light sensor 22 positioned in line with the test source 20 and connected to a printed circuit board 24.

In use, any oil mist generated by overheating of the oil 26 in the crankcase compartment 8 which may be caused by a fault in the engine is drawn by the fan 14 through the conduit 6 and into the measuring compartment 10.

During normal operation, the light source 18 is turned on and the test source 20 is turned off.

If there is any oil mist in the compartment 10, the light from the source 18 will be scattered through various angles depending on the size of the mist particles and some light will be reflected towards the light sensor 22. An amplifier on the printed circuit board 24 receives the output of the light sensor 22 and detects when the reflected light exceeds a predetermined level to provide a signal on line 28 for generating an alarm and/or stopping the engine.

The conduit 6 extends upwardly and around a U-bend before reaching the measuring compartment 10. This configuration avoids the collection of unwanted oil deposits which may otherwise collect in the measuring compartment 10. The compartment 10 is effectively an enlargement of the conduit 6, the configuration of which allows the light sources 18 and 20 and the light sensor 22 to be positioned out of the main air flow path, which further reduces the risk of unwanted oil deposits on these elements, thus increasing the reliability of the device.

The detector 2 can be tested by turning on the light source 20 and determining whether an alarm is given in response to the light sensor 22 receiving light from this source.

In the preferred embodiment, the detector has a control circuit which regularly turns on the source 20 to test the detector, and if the sensor 22 does not provide a signal indicating that light has been received, the control circuit gives an indication that the detector is not operating correctly.

The use of reflected light to indicate the presence of oil mist enhances the sensitivity of the detector. This means that the measuring compartment 10 need not be very large, and in fact the entire detector 2 can be small and compact, thus saving manufacturing costs and facilitating fixture of the device in an engine.

If desired, the conduit 6 can terminate in an aperture in the wall of the box 4, and the box 4 can be secured directly to the wall of the crankcase compartment 8 with this aperture aligned with another aperture in the crankcase wall.

I claim:

1. An oil mist detector for detecting the presence of an oil mist in an engine compartment, said detector comprising:
    means defining a measuring chamber for receiving said oil mist;
    first and second radiation source means for emitting radiation into said measuring chamber; and
    radiation sensing means, said first radiation source means and said radiation sensing means being positioned in non-aligned relationship such that said radiation sensing means is operable to sense radiation emitted from said first radiation source means and reflected by oil mist in said measuring chamber, and said second radiation source means being arranged to direct radiation to said radiation sensing means irrespective of the presence of oil mist whereby the operation of said radiation sensing means can be tested.

2. An oil mist detector as claimed in claim 1, comprising conduit means connecting said measuring chamber to said engine compartment for delivering air and oil mist thereto.

3. An oil mist detector as claimed in claim 1, including a structure defining said engine compartment, said means defining said measuring chamber comprising said engine compartment structure.

4. An oil mist detector as claimed in claim 1 wherein said radiation is infra-red radiation.

5. An oil mist detector as claimed in any one of claims 1, 2, 3 or 4, comprising means for activating an alarm when the quantity of oil mist detected exceeds a predetermined level.

6. An oil mist detector as claimed in any one of claims 1, 2, 3 or 4, including means for periodically activating said second radiation source means, and means for indicating a malfunction of the detector if the radiation sensing means does not respond to the radiation emitted by said second radiation source means.

7. An oil mist detector for detecting the presence of oil mist in an engine compartment, said detector comprising:
   means defining a measuring chamber;
   means for drawing air from said engine compartment through said measuring chamber;
   first and second radiation sources positioned to emit radiation into said measuring chamber;
   a radiation sensor disposed in such relationship with said first source that the sensor can sense radiation emitted by the first source and reflected from oil mist present in the measuring chamber, and disposed in such relationship with said second source as to receive directly radiation emitted by said second source;
   means responsive to said radiation sensor for detecting when the radiation received by said sensor exceeds a predetermined level and producing an alarm output signal; and
   alarm means responsive to said alarm output signal for providing an alarm.

8. An oil mist detector as claimed in claim 7, further comprising means for periodically operating said second radiation source, and means for indicating a malfunction of the detector if said radiation sensor does not respond to the radiation emitted by said second radiation source.

9. Oil mist detection apparatus for detecting the presence of oil mist in an engine, said engine comprising a plurality of crankcase compartments, said detection apparatus comprising a plurality of oil mist detectors, each said detector being associated with a respective one of said crankcase compartments, and comprising radiation sensing means, said sensing means being operable in the presence of oil mist in the respective crankcase compartment to sense radiation reflected from said oil mist thereby to provide an output signal indicative of the presence of said oil mist.

10. An oil mist detector as claimed in claim 9 wherein each said oil mist detector comprises first and second radiation sources, said first radiation source being positioned in non-aligned relationship with said radiation sensing means whereby the radiation sensing means can detect radiation emitted by said first radiation source and reflected from said oil mist, and said second radiation source being positioned to emit radiation directly toward said radiation sensing means.

* * * * *